United States Patent [19]

Oguma et al.

[11] 3,933,590

[45] Jan. 20, 1976

[54] METHOD OF CONTINUOUSLY CULTURING YEAST

[75] Inventors: Takeshi Oguma; Shunji Shiba; Nobuo Moritani, all of Gotsu; Yoichi Takeuchi, Hosoyama, all of Japan

[73] Assignee: Sanyo-Kokusaku Pulp Co., Ltd., Tokyo, Japan

[22] Filed: June 25, 1974

[21] Appl. No.: 482,908

[30] Foreign Application Priority Data
Nov. 6, 1973 Japan.............................. 48-124030

[52] U.S. Cl. ...................... 195/91; 195/27; 195/84; 195/94
[51] Int. Cl.²............................................ C12B 1/00
[58] Field of Search ........... 195/84, 115, 2, 118, 39, 195/82, 94, 100, 112, 91, 27

[56] References Cited
UNITED STATES PATENTS
1,680,043   8/1928   Heijkenskjold ................... 195/93 X FOREIGN PATENTS OR APPLICATIONS
847,538   9/1960   United Kingdom................... 195/82

*Primary Examiner*—A. Louis Monacell
*Assistant Examiner*—R. B. Penland
*Attorney, Agent, or Firm*—Oblon, Fisher, Spivak, McClelland & Maier

[57] ABSTRACT

Yeast is continuously cultured in a vapor condensate by adding a neutralizing agent and nutritive agents to the vapor condensate produced from the evaporation of spent sulfite liquor; inoculating said vapor condensate with Candida, Pichia or Hansenula yeast; continuously culturing said yeast in said inoculated vapor condensate; and continuously supplying unsterilized vapor condensate to control the sulfurous acid concentration and the pH of said inoculated vapor condensate.

3 Claims, No Drawings

METHOD OF CONTINUOUSLY CULTURING YEAST

BACKGROUND OF THE INVENTION

1. Field of the Invention

This invention relates to a method for the continuous culture of yeast in which the vapor condensate from spent sulfite liquor is utilized as a carbon source. More particularly, the present invention relates to a method for producing yeast such as the Candida, Pichia or Hansenula species by an industrially acceptable procedure in a medium of a vapor condensate derived from the evaporation of spent sulfite liquor and which condensate contains added nutrients.

2. Description of the Prior Art

The principal carbon sources used for producing Torula yeast in existing commercial plants are mainly xylose which is present in spent sulfite liquor, saccharides, chiefly sucrose, which are used for the production of molasses yeast such as bakers yeast, and hydrocarbons, chiefly n-paraffins, for the production of petroleum yeast. Other carbon sources such as methanol and acetic acid have been studied for the culturing of yeast.

Because protein sources have become insufficient as a result of expanding human population, the production and supply of yeast as a protein source on an industrial scale is of increasing importance. A drawback to the commercial production of yeast is that the carbon sources described above have been a source of pollution which results from the residual carbon materials present in the waste medium. Because of the pollution problem, yeast production in Japan has recently declined. Thus, it seems that it will be impossible to continue to use spent sulfite liquor in the production of Torula yeast much longer, because it will be difficult to find appropriate counter-measures to meet the government's strict standards. It also appears that it will be impossible to continue the production of yeast in molasses media because of international fluctuations in price of molasses. In the case of petroleum media, the price of n-paraffins is also unstable and is increasing because of insufficient petroleum resources. These problems regarding the cost and availability of growth media makes it difficult to produce yeast less expensively. Other factors which raise the cost of waste liquor are the treatments necessary to reduce pollution.

Under these circumstances, alternative culture media such as methanol and acetic acid have been studied. These compounds have been successfully used on a laboratory scale, but have not been found to be useful industrially in the production of yeast because of the cost of the compounds.

A need therefore, continues to exist for a method of continuously culturing yeast at relatively low cost and for a method which involves fewer pollution problems.

SUMMARY OF THE INVENTION

Accordingly, one object of the present invention is to provide a method of continuously culturing yeast by utilizing the waste liquor from the sulfite pulp process.

Briefly, this object and other objects of the present invention as hereinafter will become more readily apparent can be attained by a method of continuously culturing yeast in a vapor condensate by adding a neutralizing agent and nutritive agents to the vapor condensate produced from the evaporation of spent sulfite liquor; inoculating said vapor condensate with Candida, Pichia or Hansenula yeast; continuously culturing said yeast in said inoculated vapor condensate; and continuously supplying unsterilized vapor condensate to control the sulfurous acid concentration and the pH of said inoculated vapor condensate.

DESCRIPTION OF THE PREFERRED EMBODIMENTS

In a sulfite pulp plant, a cooking chemical solution is poured onto finely divided wood chips in a cooking kettle. After cooking, the wood chips, the solid and liquid components are separated. Thereafter, the solid components are sent to a bleaching plant. The separated liquid components are referred to as spent sulfite liquor. Since the spent liquor contains a great quantity of organic compounds which cause high COD (Chemical Oxygen Demand) and BOD (Biological Oxygen Demand) problems because of the lignin sulfonic acid and saccharides present in the liquor, it is not permitted to be discharged into rivers and the sea. The liquor is at present evaporated and is then burned wet so as to avoid pollution by discharging the liquor into public water basins. Other portions of the spent liquor are converted to various lignin products, and are also used for the production of Torula yeast.

However, the vapor condensate which is derived from the evaporation of spent sulfite liquor contains great quantities of low molecular organic compounds which originate from the wood components, and lignin sulfonic acid integrated with the splashed product upon evaporation or sulfurous compounds, which show considerably high COD and BOD values.

The low molecular weight organic compounds in the vapor condensate are 0.8 to 1.8% acetic acid, 0.05 to 0.20% formic acid, 0.03 to 0.10% furfural and 0.02 to 0.07 methanol. Further, the vapor condensate has a COD of approximately 2000 to 5000 ppm and a pH of 2. Because of these properties, the vapor condensate considerably inhibits the culturing of yeast.

A continuous series of studies have been conducted on methods of removing the sources of COD and BOD in the effluent from vapor condensate and for methods of culturing yeast on the substances in the vapor condensate which contains the growth inhibiting components. The present invention provides conditions under which yeast can be cultured in the vapor condensate. Further, the conditions are provided for the successful utilization of the vapor condensate for the culturing of yeast on an industrial scale. It has been found that the BOD and COD of waste liquor separated from yeast after culturing are greatly decreased, which confirms that the process of the invention greatly reduces the polluting effect of sulfite waste liquor.

Suitable species of yeast used for culturing include Candida, Torulopsis, Pichia and Hansenula. However, other yeast species can also be effectively cultured.

Because the vapor condensate contains growth inhibiting components, it is essential that yeast cultured in the vapor condensate develop some resistance to the medium. Normal culturing methods are preferably adopted in order to develop a resistant yeast. One method of developing a resistant strain of bacteria is described in "Biochemical Engineering" edited on December 15, 1963 by the Institute of Applied Microbiology, University of Tokyo, pp. 239–240. This report discloses the experimental results of how to impart resistance to bacteria for producing glutamic acid. The present process employs a similar technique to the above-described method. In the process, the vapor condensate is initially diluted with water by a factor of ½. Thereafter, the concentration of acetic acid is adjusted to about 1.5% by the addition of acetic acid. A nutritive agent and agar, as hereinafter is described, is then added thereto. A plate culture of yeast at 30°C is conducted, and the colonies which grow can again be cultured on the same oblique medium. The yeast which is grown can be cultured on a plate culture using undiluted vapor condensate. Thereafter the colonies which have grown can be selected therefrom as pure colonies.

Generally, a Waldhof fermenter is chiefly used for culturing yeast, and it is preferable to use this fermenter in the present invention.

To the medium used for culturing yeast, are preferably added other growth promoting components of a nitrogen source such as ammonium sulfate, ammonium nitrate, ammonium chloride, or urea, a phosphorus source such as calcium superphosphate or ammonium phosphate, and a potassium source such as potassium chloride or potassium sulfate. Other chemicals containing both potassium and phosphorus such as potassium phosphate or dipotassium phosphate can be added to the vapor condensate. Additionally, small amounts of either molasses or corn steep liquor or a mixture of both may be added as trace elements to the medium if necessary.

The vapor condensate used in this invention contains sulfurous acid which is one of the inhibitors in the vapor condensate. Therefore, after a study of the relationship between the concentration of sulfurous acid and the growth tendency of yeast in sulfurous acid containing media, it has been discovered that normal culturing cannot be conducted unless the concentration of sulfurous acid in the vapor condensate is within the range of 0.02 to 0.20%. If the concentration of sulfurous acid is less than 0.02%, when continuous culturing is conducted in a nonsterilized state, microorganisms such as mold and bacteria will grow. On the other hand, if the concentration of sulfurous acid is more than 0.20%, yeast cannot grow normally in such a medium because the concentration of sulfurous acid is too high.

In order to decrease the concentration of sulfurous acid in the vapor condensate containing over 0.20% sulfurous acid, the vapor condensate is exposed to air to aerate the growth medium. In order to increase the concentration of the sulfurous acid within the indicated limits, sulfurous acid is blown into the vapor condensate to achieve a predetermined concentration.

The continuous culturing of yeast will now be described. Vapor condensate adjusted to the appropriate concentration of sulfurous acid and a nutritive agent are charged into a fermenter. Considering the fact that the culture is in a nonsterilized state, the pH of the medium is adjusted to 4.5 to 5.5, depending upon the type of yeast.

Seed yeast previously cultured is added to the culture medium in order to start a batch culture. In the batch culture, if the pH becomes alkaline, a mineral acid such a hydrochloric acid, sulfuric acid or an organic acid such as acetic acid is added to adjust the pH. Similarly, if the pH becomes too acidic, an alkaline agent such as caustic soda or ammonia is added.

The culture is conducted at a temperature of 25°C to 35°C. When the yeast has grown to the desired concentration in the batch culture, continuous culturing is started.

In continuous culturing, the final results are not effected whether nutritive agents are added to the condensate before entering the fermenter or whether they are added separately to the fermenter.

In short, it is important in continuous culturing to control the pH of the supplied vapor condensate to within the range of 3.0 to 4.5. Generally, when the continuous culturing of the yeast is conducted using the vapor condensate, the pH of the culture medium is increased. Although a common acid may be added in order to control the pH generally, it is industrially advantageous to use the vapor condensate as the pH controlling agent because the pH of the vapor condensate is approximately 2 and it contains the carbon source for the culture. Therefore, additional vapor condensate simultaneously acts to control the pH and to supply the carbon source as well. However, if the vapor condensate is supplied at a pH below pH 3.0, great quantities of an alkaline reagent are required to adjust the pH to 4.5 to 5.5. On the other hand, if the pH of the vapor condensate supplied is over 4.5, large amounts of acid must be added to adjust the pH between 4.5 and 5.5. Therefore, it is necessary to try to balance the growth of the yeast and the pH of the supplied liquid in order to maintain the pH in the culture medium between 4.5 to 5.5 in continuous culturing. A detailed study has indicated that it is most important for culturing of the yeast to control the pH of the vapor condensate to 3.0 to 4.5.

The reasons for the allowable range of 3.0 to 4.5 are as follows:

1. The growth of yeast, of course, is influenced by the favorable and unfavorable growth conditions in the culture medium. However, the pH of the supplied vapor condensate should be controlled within the range of 3.0 to 4.5 according to the difference of the amounts of supplied liquid at that time.

2. It is necessary to add the nutritive agent into the vapor condensate in the continuous culturing of the yeast. However, when liquid ammonia is added in the necessary amount as the nitrogen source for growing the yeast, the pH of the medium is increased because of the high pH of ammonia. Since control of pH in the continuous culturing is difficult, the pH should be controlled within the range of 3.5 to 4.5. In other words, if the pH of the supplied liquid is controlled within the range of 3.0 to 4.5, the proper amount of ammonia can not only be added without extra increase in the pH, but the culturing of the yeast can be preferably conducted under favorable conditions.

Having generally described this invention, a further understanding can be obtained by reference to certain specific examples which are provided herein for purposes of illustration only and are not intended to be limiting unless otherwise specified.

EXAMPLE 1

A vapor condensate with a pH of 1.9 and a sulfurous acid concentration of 0.23% was exposed to the air at different times which aeration adjusted the concentration of sulfurous acid to approximately 0.23%, 0.2%, 0.1%, 0.02% and 0.01%, respectively. A 1.6 g amount of ammonium sulfate, 1.1 g of potassium chloride and 1 g of potassium phosphate were added to 1 liter of each sample of vapor condensate containing the different amounts of sulfurous acid. The media was adjusted to a pH of 5.0 with caustic soda solution, and then batch culturing was started in a Waldhof fermenter (volume 1 m³). The medium was not sterilized.

The seed yeast, Candida rugosa IFO 0750, used in this culture, showed resistance to the vapor condensate.

Initially, the culture was conducted as a batch process. When the dry concentration of yeast in the cultured liquid became 0.4%, it was transferred from a batch culture process to a continuous culture. The nutritive agent described above was dissolved in the supplied vapor condensate in advance, and the pH of the supplied liquid had an average pH of 3.5 (a range of 3.3 - 3.8). The pH adjustment was conducted by flowing the vapor condensate over limestone. This continuous culturing was conducted for 20 days for each sample. The dry concentration of the yeast in the stationary state, the culture cycle time and the contaminating organisms at each measurement time are shown in the following table.

|  | A | B | C | D | E |
|---|---|---|---|---|---|
| concentration of sulfurous acid (%) | 0.23 | 0.20 | 0.10 | 0.02 | 0.012 |
| Cycle time (hr.) | 5.3 | 2.8 | 2.5 | 2.5 | 2.5 |
| Dry concentration of yeast (%) | 0.28 | 0.55 | 0.57 | 0.58 | 0.43 |
| Contaminating organism (at 20 days) | none | none | none | none | mold after 1 week and impossible to culture |

As is clear from the above data, the culturing was good at a sulfurous acid concentration of 002 to 020%. It was found that the COD of the liquid after separating the yeast mycellium was 500 to 1000 ppm. It was further proved that the culturing process was effective for decreasing the COD of the vapor condensate.

EXAMPLE 2

A continuous culture of yeast in a 10 m³ Waldhof fermenter (6.5 m³ medium) was conducted using a vapor condensate having a sulfurous acid concentration of 0.08%. The nutritive agents were similar to those of Example 1 in the batch process, but ammonium sulfate was not used in the supplied liquid in the continuous culture. Instead, a 28% aqueous ammonia solution was separately added in the necessary amount. The yeast used in this study was Hansenula anomala IAM 4663 with a resistance to the vapor condensate. The pH of the vapor condensate was in the range of 3.0 to 3.6 which was adjusted with caustic soda, and the vapor condensate was cultured for 30 days. The pH of the culture was 5.3.

The dry concentration of yeast at stationary states was 0.58%, and the cycle time was 2.4 hours. Although the COD of the vapor condensate before culturing was 3800 ppm, the COD after separating yeast mycellium was 980 ppm.

EXAMPLE 3

A continuous culture was conducted for 65 days with a 1 m³ Waldhop fermenter containing 550 liters of a medium using a vapor concentrate having a sulfurous acid concentration of 0.12% at a temperature of 30°C and a pH of 5.8.

The composition of the medium was as follows.

A 1.6 g amount of ammonium chloride, 3 g of calcium superphosphate, (soluble phosphoric acid 35%), and 1.3 g of potassium sulfate were dissolved into 1 liter of vapor condensate.

The yeast used in this test was Pichia membranaefaciens HUT 7295 with a resistance to the vapor condensate. The culture was conducted by adding 30 liters of a liquid of the yeast with a concentration of 0.35% cultured in 30 liters jar fermenter.

The vapor condensate of spent sulfite liquor was adjusted to a pH of 4.5 by passing the liquor through a limestone layer. The average amount of supplied liquid was 200 liters per hour, and the cycle time was 2.7 hours.

The concentration of the yeast at this time was 0.53%, and the culture was stable and in very good condition.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method of continuously culturing yeast in a vapor condensate, comprising:
    adding a neutralizing agent and nutritive agents to the vapor condensate produced from the evaporation of spent sulfite liquor;
    inoculating said vapor condensate with a sulfurous acid resistant strain of Candida, Pichia or Hansenula yeast;
    continuously culturing said yeast in said inoculated vapor condensate at a pH of 4.5 to 5.5; and
    continuously supplying unsterilized vapor condensate to control the sulfurous acid concentration and the pH of said inoculated vapor condensate, wherein the concentration of sulfurous acid in said vapor condensate is from 0.02 to 0.20%.

2. The method of claim 1, wherein the pH of said vapor condensate is 3.0 to 4.5.

3. The method of claim 1, wherein said yeast is continuously cultured at 25° to 35°C.

* * * * *